United States Patent [19]

Hoffmann-Paquotte

[11] 4,011,234

[45] Mar. 8, 1977

[54] N-ALKANOYL OXAZOLE-CARBOXAMIDE COMPOUNDS

[75] Inventor: Hans Hoffmann-Paquotte, Inzlingen, Germany

[73] Assignee: Hoffmann-La Roche Inc., Nutley, N.J.

[22] Filed: June 25, 1976

[21] Appl. No.: 699,907

[30] Foreign Application Priority Data

July 11, 1975 Switzerland .................. 9102/75

[52] U.S. Cl. .......................... 260/307 R
[51] Int. Cl.$^2$ ...................... C07D 263/34
[58] Field of Search ................ 260/307 R

[56] References Cited

UNITED STATES PATENTS 3,222,374  12/1965  Chase ................... 260/307

*Primary Examiner*—Raymond V. Rush
*Attorney, Agent, or Firm*—Samuel L. Welt; Bernard S. Leon; Richard A. Gaither

[57] ABSTRACT

5-Cyano-4-methyl-oxazole-1,3 is prepared by pyrolyzing the reaction product of 5-carbamoyl-4-methyloxazole-1,3 and a lower alkanecarboxylic acid anhydride.

4 Claims, No Drawings

N-ALKANOYL OXAZOLE-CARBOXAMIDE COMPOUNDS

BACKGROUND OF THE INVENTION

The present invention relates to a process for the manufacture of an oxazole. More particularly, the invention is concerned with a process for the manufacture of 5-cyano-4-methyl-oxazole(1,3), which is an important intermediate in the manufacture of vitamin $B_6$.

Heretofore, 5-cyano-4-methyl-oxazole(1,3) has been obtained by reacting phosphorus pentoxide, heated to the melting point, with 5-carbamoyl-4-methyl-oxazole(1,3). This process is particularly disadvantageous in that the yields are relatively low since due to poor heat transfer, carbonization occurs quite readily.

An improvement of the aforementioned process consists in carrying out the reaction of phosphorus pentoxide with 5-carbamoyl-4-methyl-oxazole(1,3) with the addition of a solvent, namely quinoline. However, this process is disadvantageous in that quinoline is unstable under the reaction conditions, has an unpleasant odor and causes health problems. Furthermore the procedures for regenerating the quinoline and working-up the phosphorus pentoxide by-products to yield an environmentally harmless product are costly and technologically cumbersome. In addition, both quinoline and phosphorus pentoxide are expensive and not readily commercially available.

The present invention provides a process by which good quality 5-cyano-4-methyl-oxazole(1,3) is manufactured cheaply and inexpensively in high yields starting from cheap and readily accessible starting materials and without the aforementioned disadvantages of the known processes.

The objects of this invention are achieved by reacting 5-carbamoyl-4-methyl-oxazole(1,3) with a lower alkanecarboxylic acid anhydride and subjecting the reaction mixture, or optionally the 5-[N-(lower alkanoyl)-carbamoyl]-4-methyl-oxazole (1,3) isolated therefrom, to pyrolysis.

Examples of lower alkanecarboxylic acid anhydrides are the symmetrical or mixed anhydrides of straight-chain or branched-chain alkanecarboxylic acids containing up to 7 carbon atoms such as acetic anhydride, propionic anhydride, isopropionic anhydride, butyric anhydride, n-veleric anhydride, the mixed anhydrides of formic acid and acetic acid and the like. Symmetrical lower alkanecarboxylic acid anhydrides are preferably used, in particular the symmetrical anhydrides of alkane-carboxylic acids containing up to 5 carbon atoms. Acetic anhydride is particularly preferred.

In the reaction of 5-carbamoyl-4-methyl-oxazole(1,3) with a lower alkanecarboxylic acid anhydride an excess, preferably a 3 molar to 6 molar excess and in particular an approximately 5 molar excess, of lower alkanecarboxylic acid anhydride is appropriately used.

The reaction of 5-carbamoyl-4-methyl-oxazole (1,3) with a lower alkanecarboxylic acid anhydride is conveniently carried out under normal pressure and at a temperature between about 80° C. and the boiling point of the reaction mixture, preferably at the latter temperature. The reaction can also be carried out under pressure in an autoclave and at a temperature which is higher than the boiling point of the reaction mixture, for example at a temperature between about 140° C. and 250° C., preferably at a temperature between about 160° C. and 180° C., this procedure resulting in a reduction in the reaction time. After the reaction has ended, the reaction mixture contains 5-cyano-4-methyl-oxazole(1,3), excess lower alkanecarboxylic acid anhydride and lower alkanecarboxylic acid and the 5-[N-(lower alkanoyl)-carbamoyl]-4-methyl-oxazole(1,3) corresponding to the lower alkanecarboxylic acid anhydride used.

The 5-[N-(lower alkanoyl)-carbamoyl]-4-methyl-oxazole(1,3) compounds formed as intermediates in the conversion of 5-carbamoyl-4-methyl-oxazole(1,3) into 5-cyano-4-methyl-oxazole(1,3) are novel and also form part of this invention. The aforementioned intermediates are compounds of the formula:

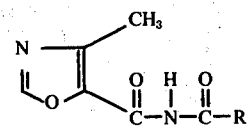

wherein R is lower alkyl. The followng can be mentioned as examples of these 5-[N-lower alkanoyl)-carbamoyl]-4-methyl-oxazole(1,3):

5-(N-acetyl-carbamoyl)-4-methyl-oxazole(1,3),
5-(N-propionyl-carbamoyl)-4-methyl-oxazole(1,3),
5-(N-n-butyryl-carbamoyl-4-methyl-oxazole(1,3)
and the like.

According to one aspect of this invention, the 5-[N-lower alkanoyl)-carbamoyl]-4-methyl-oxazole(1,3) obtained as the intermediate can be subjected to pyrolysis.

In the preferred embodiment of the present process, the reaction mixture containing the 5-[N-(lower alkanoyl)-carbamoyl]-4-methyl-oxazole(1,3) intermediate is subjected to pyrolysis. This pyrolysis is appropriately carried out under an inert gas atmosphere (e.g., nitrogen) at a temperature between about 200° C. and 600° C., preferably between about 300° C. and 500° C. and in particular at about 450° C.

The 5-[N-(lower alkanoyl)-carbamoyl]-4-methyl-oxazole(1,3) formed by reacting 5-carbamoyl-4-methyl-oxazole(1,3) with the lower alkanecarboxylic acid anhydride can also be isolated from the reaction mixture in accordance with known procedures and then subjected to pyrolysis under the conditions described hereinbefore.

Following pyrolysis, the desired 5-cyano-4-methyl-oxazole(1,3) can be isolated from the pyrolysis mixture by fractional distillation.

The present process can be carried out continuously or batchwise. It is, however, preferably carried out continuously.

According to a preferred embodiment of the present process, 5-carbamoyl-4-methyl-oxazole(1,3) is reacted with a 5 molar excess of acetic anhydride under normal pressure at about 138°–140° C. or under pressure at about 160° C. and the resulting reaction mixture is pyrolyzed at 450° C., after which 5-cyano-4-methyl-oxazole(1,3) can be isolated by distillation.

The following Examples illustrate the present invention. All temperatures are in degrees Centigrade.

EXAMPLE 1

728 g of 5-carbamoyl-4-methyl-oxazole(1,3) are dissolved in 3600 g of acetic anhydride and heated for 8 hours under reflux. The brown solution (3814 g) contains 751.4 g of 5-(N-acetyl-carbamoyl)-4-methyl-oxazole(1,3) of melting point 133° C. and 110.6 g of 5-cyano-4-methyl-oxazole(1,3).

This solution is introduced into a pyrolysis apparatus provided with a dropping funnel, thermostatically controlled at 70° C., an inlet piece for the gas inlet tube a reaction tube and a pyrolysis furnace. The reaction tube is made of glass and has a diameter of 35 mm, a total length of 65 cm and a volume when empty of 410 ml. Perforated plates of glass are fused in the tube The furnace is heated to 450° C. while being charged with nitrogen. The entire solution containing the 5-(N-acetyl-carbamoyl-4-methyl-oxazole-(1,3) and 5-cyano-4-methyl-oxazole (1,3) is then slowly added dropwise over a period of 46 hours and 30 minutes. The resulting pyrolysis product contains 579 g (92.8% of theory) of 5-cyano-4-methyl-oxazole(1,3).

EXAMPLE 2

126 g of 5-carbamoyl-4-methyl-oxazole(1,3) are dissolved in 510 g of acetic anhydride and heated for 1 hour in an autoclave at 160° C. under a pressure of 4 bars. The solution contains 78.2 g of 5-(N-acetyl-carbamoyl)-4-methyl-oxazole(1,3) and 45.8 g of 5-cyano-4-methyl-oxazole(1,3). This solution is pyrolyzed in a manner analogous to that described in Example 1. The pyrolysis product contains 97.5 g (90.2% of theory) of 5-cyano-4-methyl-oxazole(1,3).

EXAMPLE 3

126 g of 5-carbamoyl-4-methyl-oxazole(1,3) are dissolved in 510 g of acetic anhydride and heated for 30 minutes in an autoclave at 180° C. under a pressure of 5 bars. The solution contains 76.3 g of 5-(N-acetyl-carbamoyl)-4-methyl-oxazole (1,3) and 51.6 g of 5-cyano-4-methyl-oxazole(1,3). This solution is pyrolyzed in a manner analogous to that described in Example 1. The pyrolysis product contains 101.1 g (93.5% of theory) of 5-cyano-4-methyl-oxazole(1,3).

EXAMPLE 4

60.5 g of 5-carbamoyl-4-methyl-oxazole(1,3) are dissolved in 325.0 g of propionic anhydride and heated for 1 hour under reflux. The solution contains 70.3 g of 5-(N-propionyl-carbamoyl-4-methyl-oxazole(1,3) and 9.3 g of 5-cyano-4-methyl-oxazole(1,3). This solution is pyrolyzed in a manner analogous to that described in Example 1. The pyrolysis product contains 49.7 g (95.8% of theory) of 5-cyano-4-methyl-oxazole(1,3).

EXAMPLE 5

60.5 g of 5-carbamoyl-4-methyl-oxazole(1,3) are dissolved in 395.5 g of n-butyric anhydride and heated for 30 minutes under reflux. The solution contains 57.8 g of 5-(N-butyrylcarbamoyl)-4-methyl-oxazole(1,3) and 17.4 g of 5-cyano-4-methyl-oxazole(1,3). This solution is pyrolyzed in a manner analogous to that described in Example 1. The pyrolysis product contains 47.3 g (91.1% of theory) of 5-cyano-4-methyl-oxazole(1,3).

I claim:
1. A compound of the formula:

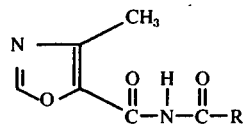

wherein R is lower alkyl.
2. The compound of claim 1 wherein said compound is 5-(N-acetyl-carbamoyl)-4-methyl-oxazole(1,3).
3. The compound of claim 1 wherein said compound is 5-(N-propionyl-carbamoyl)-4-methyl-oxazole(1,3).
4. The compound of claim 1 wherein said compound is 5-(N-butyryl-carbamoyl)-4-methyl-oxazole(1,3).

* * * * *